United States Patent
Sherwin et al.

[11] 3,934,460
[45] Jan. 27, 1976

[54] APPARATUS FOR FOCUSING AND COLLIMATING ULTRASONIC WAVES

[75] Inventors: Leo H. Sherwin, Schenectady; Robert S. Gilmore, Burnt Hills, both of N.Y.

[73] Assignee: General Electric Company, Schenectady, N.Y.

[22] Filed: Aug. 6, 1973

[21] Appl. No.: 385,893

[52] U.S. Cl. .............................. 73/71.5 US; 310/8.7
[51] Int. Cl.² ........................................ G01N 29/04
[58] Field of Search ............... 73/67.5 R, 67.6, 67.7, 73/67.8 R, 67.8 S, 67.9, 71.5 US; 310/8.1, 8.3, 8.6, 8.7, 9.1

[56] References Cited
UNITED STATES PATENTS

| | | | |
|---|---|---|---|
| 3,299,696 | 1/1967 | Dickenson | 73/71.5 US |
| 3,302,044 | 1/1967 | Lynnworth et al. | 73/67.5 R X |
| 3,309,655 | 3/1967 | Von Ardenne | 73/67.7 X |
| 3,387,604 | 6/1968 | Erikson | 73/71.5 US |
| 3,663,842 | 5/1972 | Miller | 73/67.8 X |
| 3,741,004 | 6/1973 | Posakony | 73/67.8 S |
| 3,815,409 | 6/1974 | Macouski | 73/67.9 |

FOREIGN PATENTS OR APPLICATIONS

| | | | |
|---|---|---|---|
| 732,083 | 6/1955 | United Kingdom | 73/71.5 US |

*Primary Examiner*—Richard C. Queisser
*Assistant Examiner*—John P. Beauchamp
*Attorney, Agent, or Firm*—John F. Ahern; James W. Mitchell

[57] ABSTRACT

An apparatus employing ultrasonic waves includes an ultrasonic transducer to which a solid buffer rod is attached. The ultrasonic waves are focused by liquid-filled lenses placed between the transducer and buffer rod. The ultrasonic waves are collimated by either employing a buffer rod with a spherical tip or using a plurality of liquid-filled lenses appropriately arranged. The buffer rod may be constructed of polystyrene or aluminum and the liquid-filled lenses may be constructed of glycerin or mercury, respectively. An alternative form of the invention includes a liquid-filled buffer rod and focusing and collimating means of solid materials.

19 Claims, 8 Drawing Figures

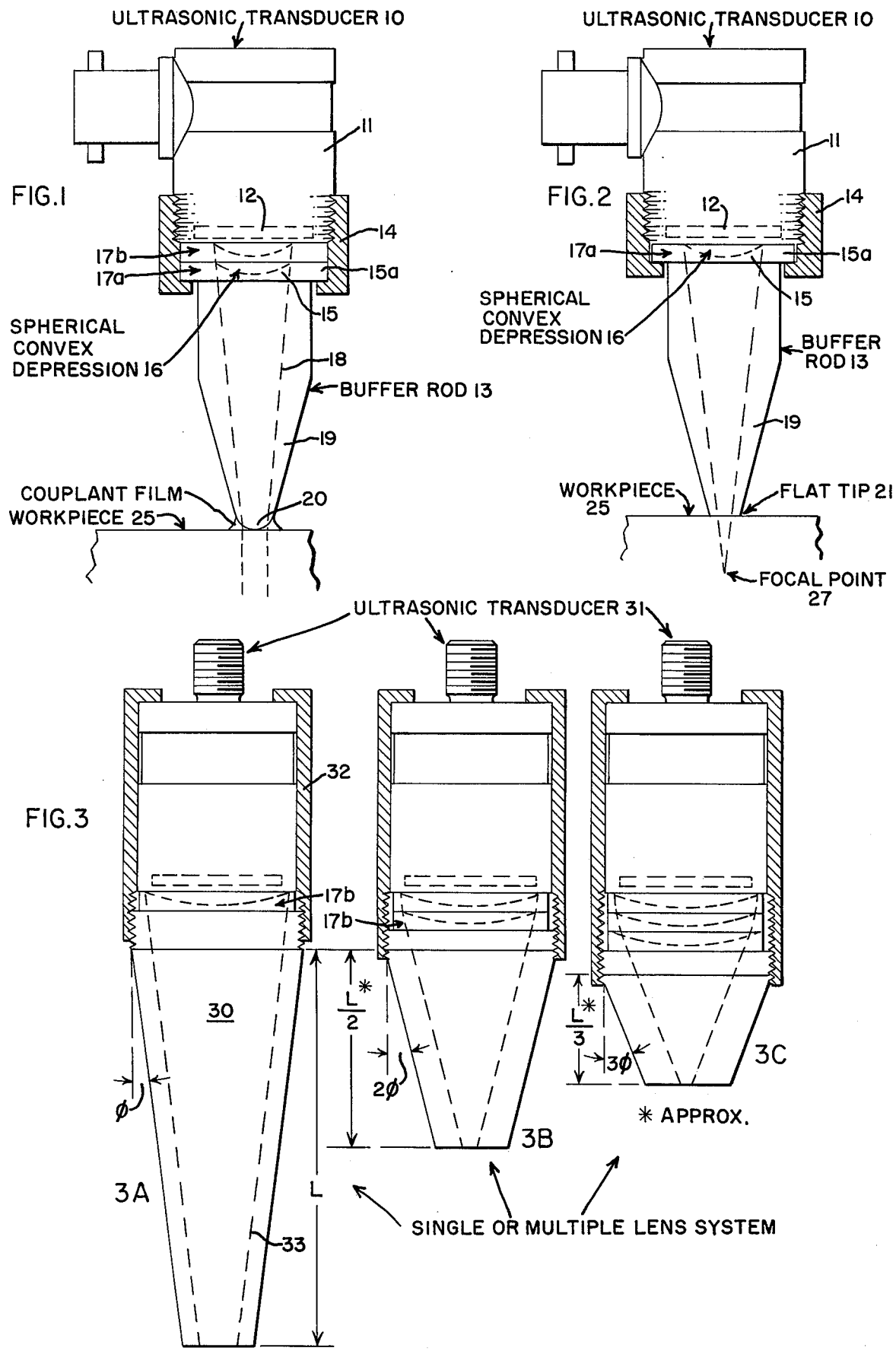

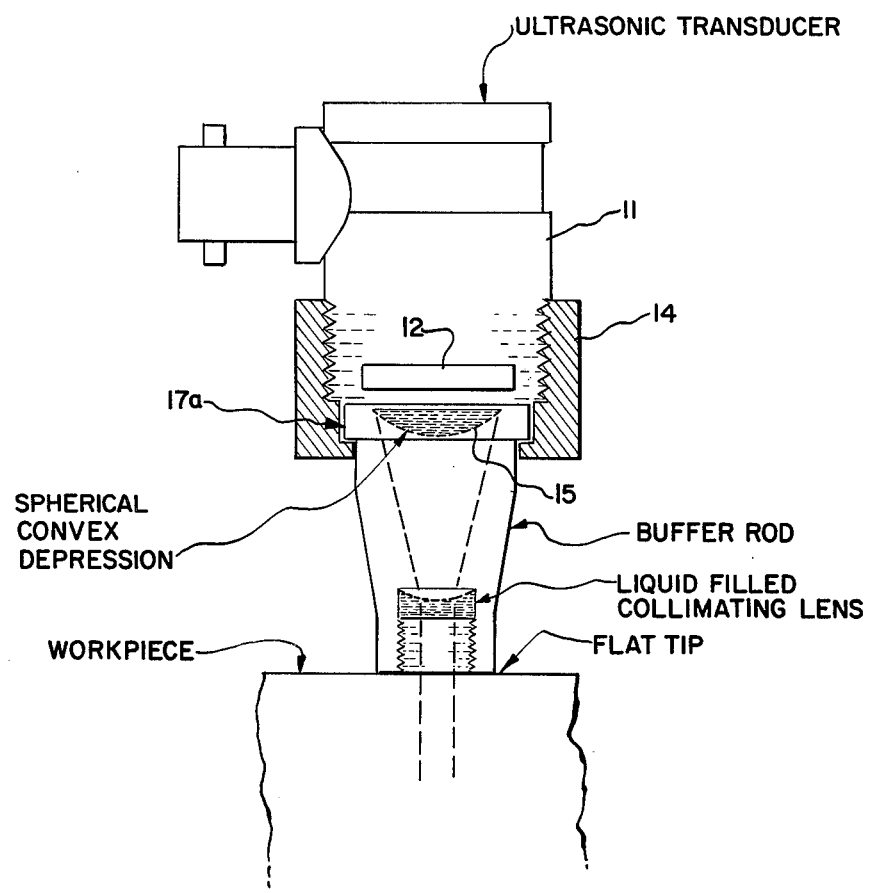

APPARATUS FOR FOCUSING AND COLLIMATING ULTRASONIC WAVES

BACKGROUND OF THE INVENTION

I. Field of the Invention

The invention is directed to a transducer apparatus and more particularly to means for focusing and collimating ultrasonic waves.

II. Description of the Prior Art

Testing systems employing ultrasonic waves are well known. These systems are generally of two types: contact testing systems in which a transducer for generating ultrasonic waves contacts a workpiece and the waves are transmitted through a liquid couplant layer, and immersion testing systems in which the transducer is spaced apart from the workpiece and the waves are transmitted into the workpiece through an intervening liquid in which the workpiece and transducer are immersed. Although it is possible with immersion testing to produce a narrow, focused, collimated beam of ultrasonic waves, efforts to realize such a result with contact testing generally have been unsuccessful.

Mere focusing of a rather large beam is possible with contact testing. Prior art devices generally employ a tube containing a column of water or other suitable fluid coupled to the transducer. An appropriate focusing device, such as a lens is disposed intermediate the transducer and the tube containing the water. The tube may be either sealed with a thin membrane at the end nearest a workpiece or the end nearest the workpiece may be open and a continuous flow of water may be discharged against the workpiece. There are many disadvantages with this type of testing. The amount of focusing obtainable is quite limited and in the second alternative mentioned above, the workpiece and surrounding area are exposed to a flow of water. Additionally, the lowest $f$ number achievable is about 1.4. A further serious drawback is that this type of contact testing cannot produce a collimated beam of ultrasonic waves, which collimated beam of ultrasonic waves may be desirable for some test purposes.

To achieve high energy output and good sensitivity, prior art contact testing devices have relied on large transducers. However, the contact area of such transducers is very large. Further, the large beam produced by such large transducers makes testing more difficult, since the reflective area of a discontinuity is only a small percentage of the area of the cross-section of the beam.

In view of the above-mentioned problems, it is an object of the invention to provide an apparatus wherein a narrow, focused, collimated beam of ultrasonic waves is produced.

It is a further object of the invention to provide a focused and collimated beam of ultrasonic waves without using a coupling medium as the beam-forming vehicle.

It is another object of the invention to provide a contact testing apparatus wherein a focused and collimated beam of ultrasonic waves is produced and in which the beam forming vehicle need not contact the workpiece or the area surrounding the workpiece.

It is a still further object of the invention to provide a portable contact testing device.

SUMMARY OF THE INVENTION

In carrying out the invention, in one form thereof, an apparatus employing ultrasonic waves is disclosed wherein a transducer for generating ultrasonic waves is disposed within a housing. In order to direct the ultrasonic waves to a desired position, a buffer rod of polystyrene or aluminum is coupled to the transducer. Intermediate the buffer rod and transducer, however, is disposed at least one lens element filled with a liquid, which liquid may be either glycerin or mercury. The buffer rod is provided with a converging tip in the form of a spheroid for collimating the ultrasonic waves. Another form of the invention includes a liquid-filled buffer rod and focusing and collimating means of solid materials.

DESCRIPTION OF THE DRAWINGS

FIG. 1 is a schematic view of apparatus according to the invention showing a plurality of liquid-filled lens elements and a buffer rod provided with a converging tip.

FIG. 2 is a schematic view similar to that of FIG. 1, but with a single liquid-filled lens element and a buffer rod provided with a flat tip.

FIGS. 3A, 3B, and 3C are schematic views similar to that of FIG. 2, but showing the use of one or more liquid-filled lens elements with a buffer rod having a flat tip.

FIG. 6 is a schematic view of the apparatus according to the present invention wherein there is a liquid filled focusing lens and a liquid filled collimating lens in combination with a solid flat-tipped buffer rod.

DESCRIPTION OF THE INVENTION

Figure 4:
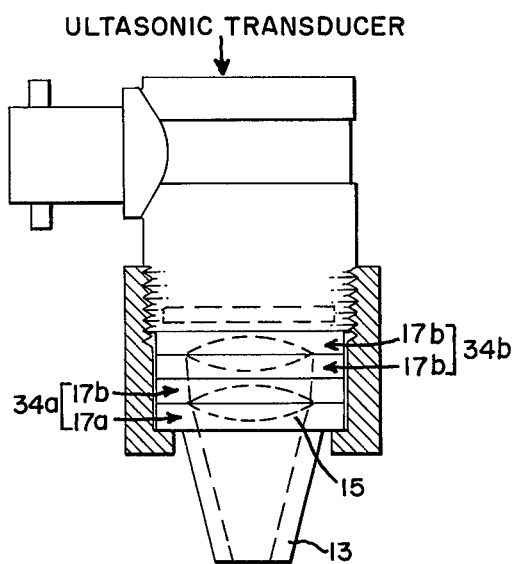
FIG. 4 is a schematic view similar to FIG. 2, with a plurality of liquid-filled lens elements arranged to form a plurality of liquid-filled, double convex spherical lenses.

Referring to FIG. 1, an ultrasonic transducer 10 is shown which includes a housing 11 within which an active element 12 is disposed. The transducer may be one of any well-known, commercially available types. Integrally formed with a buffer rod 13 is a first disk-like member 15 having a flanged portion 15a and including a spherical convex depression 16. When filled with a suitable liquid, convex depression 16 forms a lens element 17a. Buffer rod 13 is coupled to transducer 10 by collar 14 which engages flange 15a and threadably engages housing 11. A second, single lens element 17b is shown stacked above disk-like member 15 and adjacent active element 12. Lens element 17b is formed of the same material as buffer rod 13 and contains a spherical convex depression of the type of spherical convex depression 16. Thus, either a single or multiple liquid-filled lens capability may be provided merely by stacking disk-like lens elements atop disk-like member 15 prior to coupling buffer rod 13 to transducer 10.

Collimating of the ultrasonic waves generated by active element 12, which waves are indicated as bounded by dashed lines at 18, is accomplished by reducing buffer rod 13 to a converging tip 19 in the form of a spheroid 20. Intermediate a workpiece 25 and spherical tip 20 is disposed a couplant film 26. These elements combine to form a plano-concave collimating lens which collimates the focused waves.

Many advantages accrue to the above-described system. The testing apparatus may be fabricated as a portable apparatus so that it may be carried from workpiece to workpiece. No immersion of the transducer and workpiece is required, nor is a flow of water employed. To utilize the apparatus incorporating the invention, in practice, it is only necessary to use a thin layer of couplant with the apparatus, which apparatus produces a collimated beam of utlrasonic waves. The couplant is not required to be the beam forming vehicle, nor is the beam forming vehicle in contact with the workpiece. This is because the liquid-filled focusing means are isolated from the workpiece, being securely disposed between buffer rod 13 and transducer 10.

FIG. 2 shows the apparatus of FIG. 1 with certain distinguishing features. First, only a single lens element 17a is provided. As before, this lens element comprises disk-like member 15 with spherical convex depression 16, which depression is filled with a liquid. At the other end of buffer rod 13, converging portion 19 does not reduce to a spherical tip, but is ground flat at 21. In use, a thin uniform couplant film is provided and the ultrasonic waves pass directly through workpiece 25 to a focal point 27. This apparatus produces a focused, but not collimated beam of ultrasonic waves.

An alternative form of construction is shown in FIGS. 3A, 3B, and 3C wherein the length of a buffer rod 30 may be changed according to the number of lens elements employed. It is seen that this configuration may also employ a disk-like member integrally formed with buffer rod 30, and threadably couples buffer rod 30 to transducer 31 by means of overlying collar 32. In order to reduce spurious boundary interference, it is desirable to contain the ultrasonic waves within that area shown by dashed lines 33 of FIG. 3A. Thus, an appropriate converging angle $\phi$ is shown, which converging angle $\phi$ is related to the focusing power of liquid-filled lens element 17b. Referring to FIG. 3B, it is possible to shorten buffer rod 13 by one-half, provided a second lens element is added and converging angle $\phi$ is increased to 2 $\phi$. Similarly, in FIG. 3B, buffer rod 13 is one-third its original length with the addition of a third lens element and the increase of converging angle $\phi$ to 3 $\phi$. Other relative lens structures and converging angles may be employed as dictated by the particular use to which the apparatus incorporating the invention is to be put. This system provides excellent versatility and is capable of being matched to virtually any testing requirements.

A different arrangement of lens elements 17a and 17b is shown in FIG. 4. A buffer rod similar to the buffer rod 13 of FIG. 1 and utilizing the same reference numbers hereat is employed with its disk-like member 15 integrally formed therewith. A series of single lens elements 17b is stacked atop disk-like member 15, but are arranged face-to-face to form two, double convex, spherical, liquid-filled lenses 34a and 34b.

Figure 5:
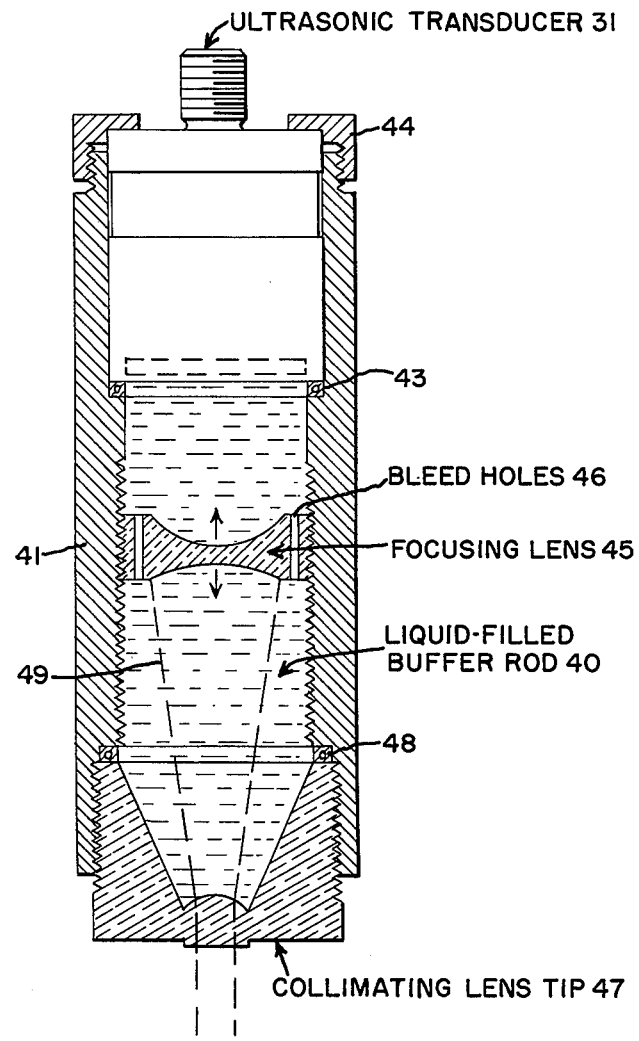
FIG. 5 is a schematic view of another form of the apparatus according to the invention wherein a liquid-filled buffer rod is coupled to a transducer and both focusing and collimating are carried out by solid lens elements.

An alternative embodiment of the invention is shown in FIG. 5. The same transducer, housing, and active element shown in FIGS. 3A, 3B, and 3C are employed in this embodiment. However, a liquid-filled buffer rod 40 is employed in place of the solid buffer rod 30. This is accomplished by cylindrical means 41 which forms a liquid-tight seal with transducer 31 by means of O-ring 43. Cylindrical means 41 is held in place by flanged collar 44. A solid focusing lens 45 containing bleed holes 46 is translatably disposed within cylindrical means 41. Liquid within cylindrical means 41 is retained therein by collimating lens tip 47 which threadably engages cylindrical means 41 and makes a liquid-tight seal by means of O-ring 48. In operation, cylindrical means 41 is filled with liquid after focusing lens 45 has been adjusted to an appropriate position. Collimating lens tip 47 is screwed into cylindrical means 41 to retain the liquid therein. Ultrasonic waves generated by transducer 31 are directed through liquid-filler buffer rod 40 and are focused by focusing lens 45. The waves are indicated as bounded by dashed lines as at 49. Collimation of these waves is effected by collimating lens tip 47. As with other forms of the invention, this apparatus may be made portable and requires no immersion of the apparatus and workpiece, nor is a flow of liquid against the workpiece or the area surrounding the workpiece required. As with the first-mentioned embodiment, the coupling medium is not employed as a beam-forming vehicle, nor is the beam-forming vehicle in contact with the workpiece.

The particular materials employed with the invention are important and comprise a portion of the invention itself. In order to eliminate internal reflections within the lens and buffer rod, the invention requires that the acoustic impedance of the liquid within the lenses and the acoustic impedance of the solid material of the buffer rod and lens elements be very closely matched. One liquid-solid combination discovered by the inventors to work very well is glycerin-polystyrene. The planar interference reflection coefficient of these material is 0.003, which means that they are essentially non-reflecting. However, the minimum $f$ number achievable is somewhat high at about 2.65. The invention overcomes this apparent defect by employing multiple lenses which reduce the $f$ number of such a non-reflective lens system. Other advantages of this system include the capability to vary the focus by changing lens elements and the reduction of interference caused by spurious modes and echoes by utilizing viscous damping. Interference is also reduced by focusing the ultrasonic waves away from the buffer rod boundaries.

Another liquid-solid combination with excellent acoustic impedance characteristics is mercury-aluminum. The planar interference reflection coefficient of this combination is 0.06, which is more reflective than the glycerin-polystyrene combination. However, the index of refraction for mercury-aluminum is 4.40 compared to 1.23 for glycerin-polystyrene, showing that mercury-aluminum is a more efficient lens. Additionally, the minimum $f$ number achievable with mercury-aluminum is 0.65. The above-mentioned materials apply equally well whether the liquid is employed within a lens, or, as shown in FIG. 5, within a buffer rod. Conversely, the solid materials work equally well whether employed in a buffer rod or, as shown in FIG. 5, in a focusing or collimating lens.

Although not specifically illustrated, many combinations of elements will be obvious to those skilled in the art. For example, liquid-filled lenses may be used at either end of a solid buffer rod, either singly or in multiples. Collimating may be accomplished not only by a converging buffer rod with a spheroid tip but may be done with a plurality of liquid-filled lenses in conjunction with a flat-tipped buffer rod. With a liquid buffer rod as shown, for example, in FIG. 6, a plurality of translatable solid lenses may be used.

While several specific embodiments of the invention have been described, it will be obvious to those skilled in the art that changes and modifications may be made without departing from the invention. Illustrative of this are the lastly mentioned examples, which are not intended to be by way of limitation. It is therefore intended in the appended claims to cover all such changes and modifications that fall within the true spirit and scope of the invention.

We claim:

1. An ultrasonic testing apparatus comprising a transducer including a planar active element for generating ultrasonic waves; focusing means adjacent said transducer for focusing said ultrasonic waves, said focusing means comprising at least one liquid-filled lens element; and, a buffer rod for transmitting said focused ultrasonic waves to a test piece without requiring said apparatus or test piece to be submerged in a liquid; wherein, said buffer rod is comprised of polystyrene and said liquid-filled lens element is comprised of glycerin.

2. An ultrasonic testing apparatus comprising a transducer including a planar active element for generating ultrasonic waves; focusing means adjacent said transducer for focusing said ultrasonic waves, said focusing means comprising at least one liquid-filled lens element; and, a buffer rod for transmitting said focused ultrasonic waves to a test piece without requiring said apparatus or test piece to be submerged in a liquid; wherein, said buffer rod is comprised of aluminum and said liquid-filled lens element is comprised of mercury.

3. An ultrasonic testing apparatus comprising a transducer including a planar active element for generating ultrasonic waves; focusing means adjacent said transducer for focusing said utlrasonic waves, said focusing means comprising a plurality of liquid-filled lens elements arranged to provide at least one liquid-filled double convex lens; and, a buffer rod for transmitting said focused utlrasonic waves to a test piece without requiring said apparatus or test piece to be submerged in a liquid; wherein, said buffer rod is comprised of polystyrene and said liquid-filled lens elements are comprised of glycerin.

4. An ultrasonic testing apparatus comprising a transducer including a planar active element for generating ultrasonic waves; focusing means adjacent said transducer for focusing said ultrasonic waves, said focusing means comprising a plurality of liquid-filled lens elements arranged to provide at least one liquid-filled double convex lens; and, a buffer rod for transmitting said focused ultrasonic waves to a test piece without requiring said apparatus or test piece to be submerged in a liquid; wherein said buffer rod is comprised of aluminum and said liquid-filled lens elements are comprised of mercury.

5. An ultrasonic testing apparatus for transmitting ultrasonic waves to a workpiece comprising:
a housing including a transducer comprising a planar active element for generating ultrasonic waves;
a buffer rod attached to said housing for contacting said workpiece; and,
means for focusing said ultrasonic waves, said focusing means disposed between said transducer and the end of the rod remote from the contact end of said buffer rod; said focusing means including at least one lens element having at least one liquid-filled depression and the acoustic impedance of the liquid closely matches the acoustic impedance of the buffer rod, said ultrasonic waves being transmitted to said workpiece without requiring said apparatus or the workpiece to be submerged in a liquid.

6. An ultrasonic testing apparatus for transmitting ultrasonic waves to a workpiece comprising:
a housing including a transducer comprising a planar active element for generating ultrasonic waves;
a liquid-filled buffer rod coupled to said transducer for directing said ultrasonic waves to a desired position; and,
focusing means disposed within said liquid-filled buffer rod for focusing said ultrasonic waves, said liquid-filled buffer rod having a solid lens tip at the contact end thereof for collimating said ultrasonic waves.

7. The apparatus of claim 5 wherein said buffer rod is comprised of polystyrene and said liquid-filled lens element is comprised of glycerin.

8. The apparatus of claim 5 wherein said buffer rod is comprised of aluminum and said liquid-filled lens element is comprised of mercury.

9. The apparatus of claim 5 wherein there are a plurality of liquid-filled lens elements arranged to provide at least one liquid-filled double convex lens.

10. The apparatus of claim 9 wherein said buffer rod is comprised of polystyrene and said liquid-filled lens elements are comprised of glycerin.

11. The apparatus of claim 9 wherein said buffer rod is comprised of aluminum and said liquid-filled lens elements are comprised of mercury.

12. Ultrasonic testing apparatus comprising a transducer including a planar active element for generating ultrasonic waves; a buffer element containing at least one enclosed liquid-filled lens element for focusing said ultrasonic waves without requiring said apparatus or an object being tested to be submerged in a liquid; and means for collimating said focused ultrasonic waves prior to impingement upon a test sample.

13. The apparatus of claim 12 wherein said collimating means comprises a rounded spherical tip on said buffer means adapted to form with a couplant liquid film a collimating lens.

14. The apparatus of claim 12 wherein said collimating means comprises at least one collimating enclosed liquid-filled lens within said buffer means at the end thereof remote from said tranducer.

15. The apparatus of claim 12 wherein said buffer rod is comprised of polystyrene and said liquid-filled lens element is comprised of glycerin.

16. The apparatus of claim 12 wherein said buffer rod is comprised of aluminum and said liquid-filled lens element is comprised of mercury.

17. The apparatus of claim 4 wherein said focusing means comprise at least one solid lens element.

18. The apparatus of claim 17 wherein said solid lens element is capable of translation within said liquid-filled buffer rod.

19. The apparatus of claim 17 wherein said liquid-filled buffer rod contains glycerin and said solid lens element and said solid lens tip comprise polystyrene.

* * * * *